US012571763B2

(12) United States Patent
Chen

(10) Patent No.: US 12,571,763 B2
(45) Date of Patent: Mar. 10, 2026

(54) DETECTION METHOD FOR LOW-CONCENTRATION METAL IONS IN SOLUTION

(71) Applicant: NATIONAL CENTRAL UNIVERSITY, Taoyuan (TW)

(72) Inventor: Wen-Yih Chen, Taoyuan (TW)

(73) Assignee: NATIONAL CENTRAL UNIVERSITY, Taoyuan City (TW)

( * ) Notice: Subject to any disclaimer, the term of this patent is extended or adjusted under 35 U.S.C. 154(b) by 274 days.

(21) Appl. No.: 18/238,518

(22) Filed: Aug. 27, 2023

(65) Prior Publication Data

US 2024/0085367 A1 Mar. 14, 2024

Related U.S. Application Data

(60) Provisional application No. 63/405,437, filed on Sep. 11, 2022.

(51) Int. Cl.
| | |
|---|---|
| *G01N 27/414* | (2006.01) |
| *G01N 1/28* | (2006.01) |
| *G01N 1/38* | (2006.01) |
| *G01N 33/20* | (2019.01) |

(52) U.S. Cl.
CPC ............. *G01N 27/414* (2013.01); *G01N 1/28* (2013.01); *G01N 1/38* (2013.01); *G01N 27/4146* (2013.01); *G01N 33/20* (2013.01); *G01N 2001/2893* (2013.01)

(58) Field of Classification Search
CPC .......... G01N 27/414; G01N 1/28; G01N 1/38; G01N 27/4146; G01N 33/20; G01N 2001/2893
See application file for complete search history.

(56) References Cited

U.S. PATENT DOCUMENTS

| | | | | |
|---|---|---|---|---|
| 8,628,650 B2 * | 1/2014 | Ah | ..................... | G01N 27/4145 204/644 |
| 8,828,138 B2 * | 9/2014 | Bedell | .................... | B82Y 15/00 117/2 |
| 2002/0138505 A1 * | 9/2002 | Fabrizio | ................... | G01K 7/01 |
| 2003/0218194 A1 * | 11/2003 | Chou | ................... | G01N 27/414 257/288 |

(Continued)

FOREIGN PATENT DOCUMENTS

| | | | | |
|---|---|---|---|---|
| CN | 101051038 A | * | 10/2007 | ............. E01H 11/00 |
| CN | 108535470 A | * | 9/2018 | ............. G01N 33/53 |
| TW | 591227 B | * | 6/2004 | |

OTHER PUBLICATIONS

CN-101051038-A, English Translation (Year: 2007).*

(Continued)

*Primary Examiner* — Ryan D Walsh
(74) *Attorney, Agent, or Firm* — Cheng-Ju Chiang

(57) ABSTRACT

The present invention discloses a detection method for low-concentration metal ions in solution, which avoids damage of strong acids and strong alkalis to the field effect transistors (FET) while using a control solution as a reference for calibration. By adjusting the electronic signals (resistance, inductance, current, voltage, etc.) generated by the solution to be tested and the control solution to be the same, the voltage difference therebetween is employed to quantitively infer the metal ions concentration of the solution to be tested.

7 Claims, 6 Drawing Sheets

200

(56) References Cited

U.S. PATENT DOCUMENTS

2005/0156584 A1* 7/2005 Feng ................... G01N 27/414
                                                    257/253
2017/0082570 A1* 3/2017 Takechi ............. G01N 27/4145
2021/0293798 A1* 9/2021 Kornberg .......... G01N 27/4145

OTHER PUBLICATIONS

CN-108535470-A, English Translation (Year: 2018).*
TW-591227-B, English Translation (Year: 2004).*
Parizi et al (ISFET pH Sensitivity: Counter-Ions Play a Key Role; Scientific Reports 7:41305 | DOI: 10.1038/srep41305; Published Feb. 2, 2017) (Year: 2017).*
Bazylewski et al (Solid-State Chemiresistors from Two-Dimensional MoS2 Nanosheets Functionalized with L Cysteine for In-Line Sensing of Part-Per-Billion Cd2+ Ions in Drinking Water; DOI: 10.1021/acsomega.9b03246 ACS Omega 2020, 5, 643-649; Published 2020) (Year: 2020).*
Falina et al . (Ten Years Progress of Electrical Detection of Heavy Metal Ions (HMIs) Using Various Field-Effect Transistor (FET) Nanosensors: A Review; Biosensors 2021, 11, 478. https://doi.org/10.3390/bios11120478; Published Nov. 25, 2021) (Year: 2021).*

* cited by examiner

Ag/AgCl

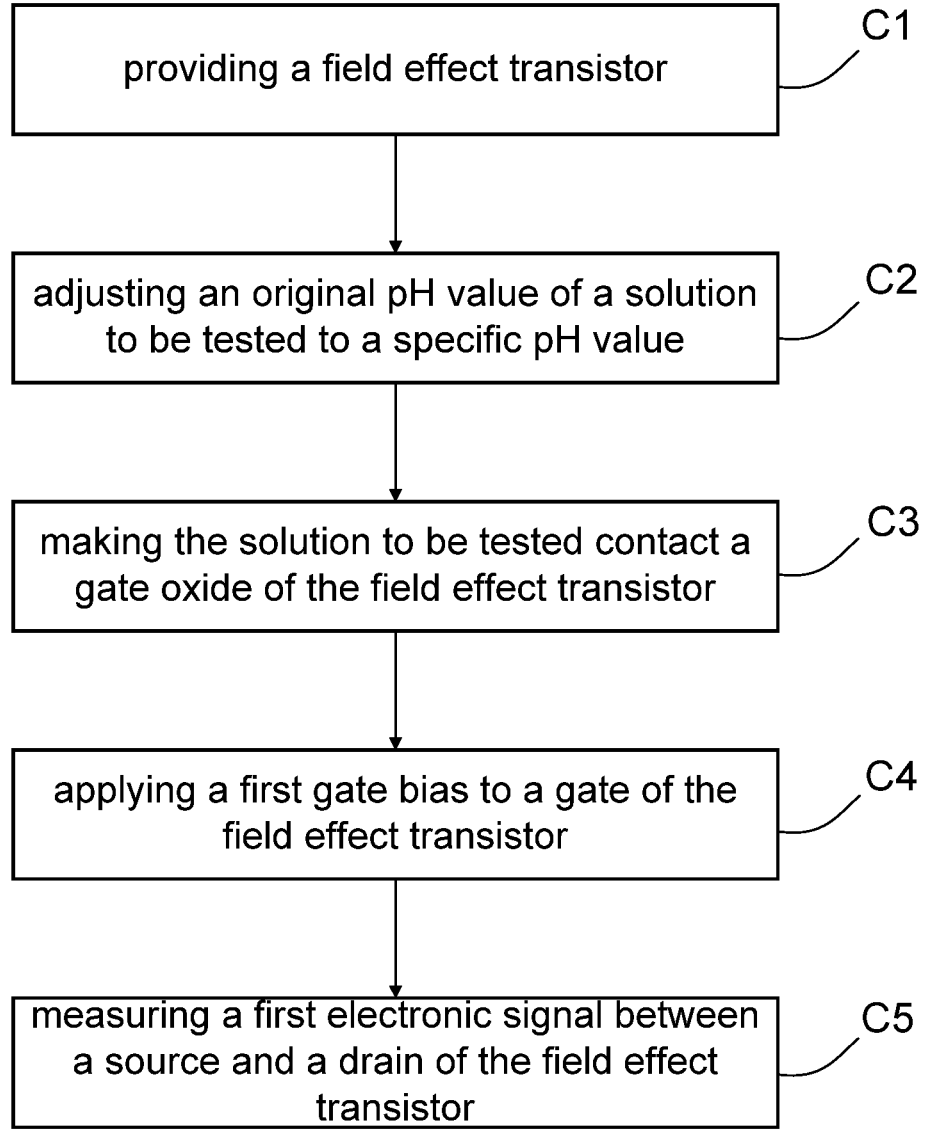

providing a field effect transistor — C1 adjusting an original pH value of a solution to be tested to a specific pH value — C2 making the solution to be tested contact a gate oxide of the field effect transistor — C3 applying a first gate bias to a gate of the field effect transistor — C4 measuring a first electronic signal between a source and a drain of the field effect transistor — C5

FIG. 4

DETECTION METHOD FOR LOW-CONCENTRATION METAL IONS IN SOLUTION

CROSS REFERENCE TO RELATED APPLICATIONS

The present invention claims benefit of U.S. Provisional Application No. 63/405,437, filed on Sep. 11, 2022, the disclosure of which is incorporated by reference herein.

FIELD OF THE INVENTION

The present invention relates to a detection method for low-concentration metal ions in solution, particularly chemistry detection in the solutions used in the semiconductor industry.

BACKGROUND OF THE INVENTION

Many chemicals need to be used in the existing semiconductor manufacturing processes. Meanwhile, whether the metal ion (such as iron ion) in the chemicals is over the AQL (Acceptable Quality Level) or not is detected commonly by an inductively coupled plasma mass spectrometry (ICP-MS) or atomic absorption spectroscopy (AA). However, the limit of detection concentration is only in the range of ppt ($10^{-12}$ Molar), and, unfortunately, the chemicals containing metal ions concentration lower than that can be a hurdle for raising the production yield in high-end semiconductor chip manufacturing. Moreover, ICP-MS and AA are expensive instruments requiring highly trained personnel. Although ICP-MS and AA can do qualitative analysis, quantitative analysis will fail to measure lower concentrations below the detection limitation. Furthermore, in fact, as long as the metal ion's concentration reaches ppq ($10^{-15}$ Molar) in the chemicals used in the manufacturing processes, defects will be occurred and downgrade the production yield in the products (such as semiconductor chip and components, etc.).

Although utilization of the characteristics of field effect transistors (FET) exists for detecting the metal ions concentrations of solutions, particularly for environmental detection, most of them can only process aqueous solutions (i.e., the pH (potential of Hydrogen ion) value is between 6-8 and water is used as the solvent). For solutions with high acidity and alkalinity (pH value greater than or equal to 9, or is less than or equal to 4), and particularly for organic solutions, there is no effective quantitative metal ions detection method.

Dilution can reduce the influence of solution pH value, but it will make the detection for metal ions of already low-concentration more difficult.

Therefore, the detection of low-concentration metal ions is restricted by the concentration, and no so-called standard substance exists in the common detections as a reference for calibration. A technical issue that urgently needs to be solved is how to measure the metal ions quantitively in the solution to be tested more properly in a limitation of low-concentration.

Moreover, non-specific adsorption during the detection process of the sensor is troublesome. False signals would be generated if any non-target molecules or ions in the sample are adsorbed on the sensor.

Meanwhile, there are also technical issues to solve: how to increase the sensitivity of the sensor for metal ions and the sensitivity of the specific adsorption for the specific metal ions.

Therefore, there is a need to provide a detection method for low-concentration metal ions to solve the aforementioned technical problems.

SUMMARY OF INVENTION

In order to solve the problems of the aforementioned prior art, the present invention provides a detection method for low-concentration metal ions in solution, which avoids damage of strong acids and strong alkalis to the field effect transistors (FET) while using a control solution as a reference for calibration. By adjusting the electronic signals (resistance, inductance, current, voltage, etc.) generated by the solution to be tested and the control solution, the voltage difference therebetween is employed to quantitively and properly infer the metal ions concentration of the solution to be tested.

To realize the aforesaid objective, the present invention provides a detection method for low-concentration metal ions in solution: first, providing a field effect transistor; then, adjusting an original pH value of a solution to be tested to a specific pH value; then, making the solution to be tested contact a gate oxide of the field effect transistor with or without modifications; then, applying a first gate bias to a gate of the field effect transistor; then, measuring a first electronic signal between a source and a drain of the field effect transistor.

In a preferred embodiment, the solution to be tested comprises an organic solvent.

In a preferred embodiment, the original pH value of the solution to be tested is greater than or equal to 9, or is less than or equal to 4.

In a preferred embodiment, the field effect transistor is selected from a group consisting of a carbon nanotube field effect transistor, a graphene field effect transistor, a nanoplate field effect transistor, and a nanowire field effect transistor.

In a preferred embodiment, the solution to be tested is adjusted to a specific temperature range.

In a preferred embodiment, the specific temperature range is 10° C.-80° C.

In a preferred embodiment, the detection method further comprises steps of: first, adjusting an original pH value of a control solution to the specific pH value; then, making the control solution contact the gate oxide of the field effect transistor; then, applying a second gate bias to the gate of the field effect transistor; then, measuring a second electronic signal between the source and the drain of the field effect transistor.

In a preferred embodiment, the detection method further comprises steps of: adjusting the first gate bias and the second gate bias until the first electronic signal is equal to the second electronic signal, subtracting the second bias from the first bias to obtain a voltage difference; then, judging a metal ions concentration of the solution to be tested according to the voltage difference.

To realize the aforesaid objective, the present invention further provides a detection method for low-concentration metal ions in solution: first, providing a field effect transistor; then, adjusting an original pH value of a solution to be tested to a specific pH value; then, making the solution to be tested contact a gate oxide of the field effect transistor; then, applying a first gate bias to a gate of the field effect transistor; then, measuring a first electronic signal between a source and a drain of the field effect transistor, wherein a first functional group for attracting or adsorbing metal ions of the solution to be tested and a second functional group for resisting non-specific adsorption are arranged on the gate oxide.

In a preferred embodiment, the original pH value of the solution to be tested is greater than or equal to 9, or is less than or equal to 4.

In a preferred embodiment, the detection method further comprises steps of: first, adjusting an original pH value of a control solution to the specific pH value; then, making the control solution contact the gate oxide of the field effect transistor; then, applying a second gate bias to the gate of the field effect transistor; then, measuring a second electronic signal between the source and the drain of the field effect transistor.

In a preferred embodiment, the detection method further comprises steps of: adjusting the first gate bias and the second gate bias until the first electronic signal is equal to the second electronic signal; subtracting the second bias from the first bias to obtain a voltage difference; judging a metal ions concentration of the solution to be tested according to the voltage difference.

Compared with the prior arts, the present invention avoids damage of strong acids and strong alkalis to the field effect transistors (FET) while using a control solution as a reference for calibration. By adjusting the electronic signals (resistance, inductance, current, voltage, etc.) generated by the solution to be tested and the control solution to be the same, the voltage difference therebetween is employed to quantitively and properly infer the metal ions concentration of the solution to be tested.

BRIEF DESCRIPTION OF THE ACCOMPANYING DRAWINGS

FIG. 4 is a flowchart illustrating a detection method for low-concentration metal ions in solution according to the first preferred embodiment of the present invention;

DETAILED DESCRIPTION OF PREFERRED EMBODIMENTS

The following descriptions of the embodiments refer to the appended figures to illustrate specific embodiments in which the present application may be implemented. The directional terms of up, down, front, rear, left, right, interior, exterior, side, etcetera mentioned in the present application are merely directions of referring to appended figures. Therefore, the aforesaid directional terms are employed for explaining and understanding the present application, but the present application is not limited thereto.

Figure 1:
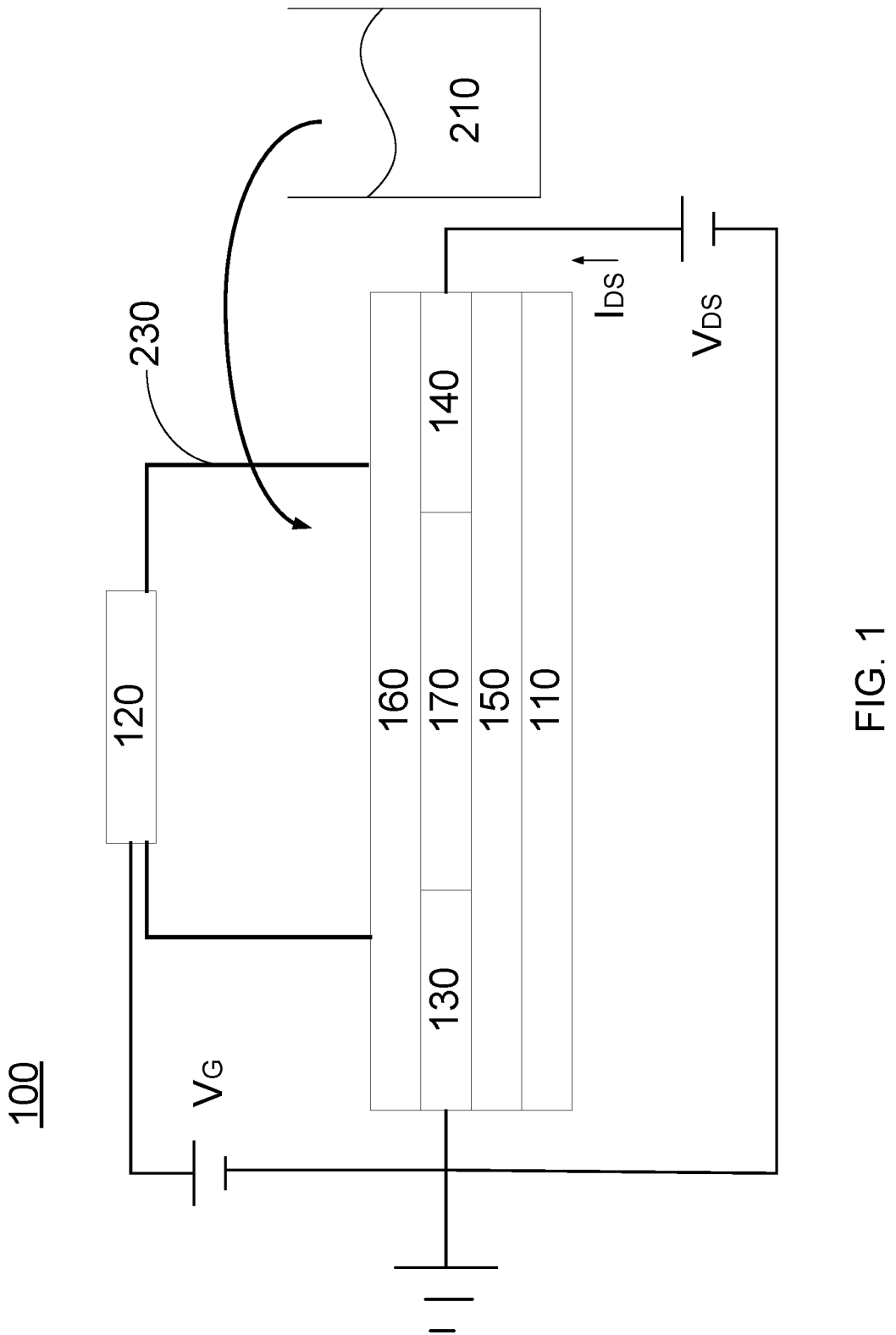
FIG. 1 shows a schematic diagram of the operation of the detection method for low-concentration metal ions in solution according to the first preferred embodiment of the present invention.
Figures 2A, 2B, 2C, 2D, 2E, 2F:
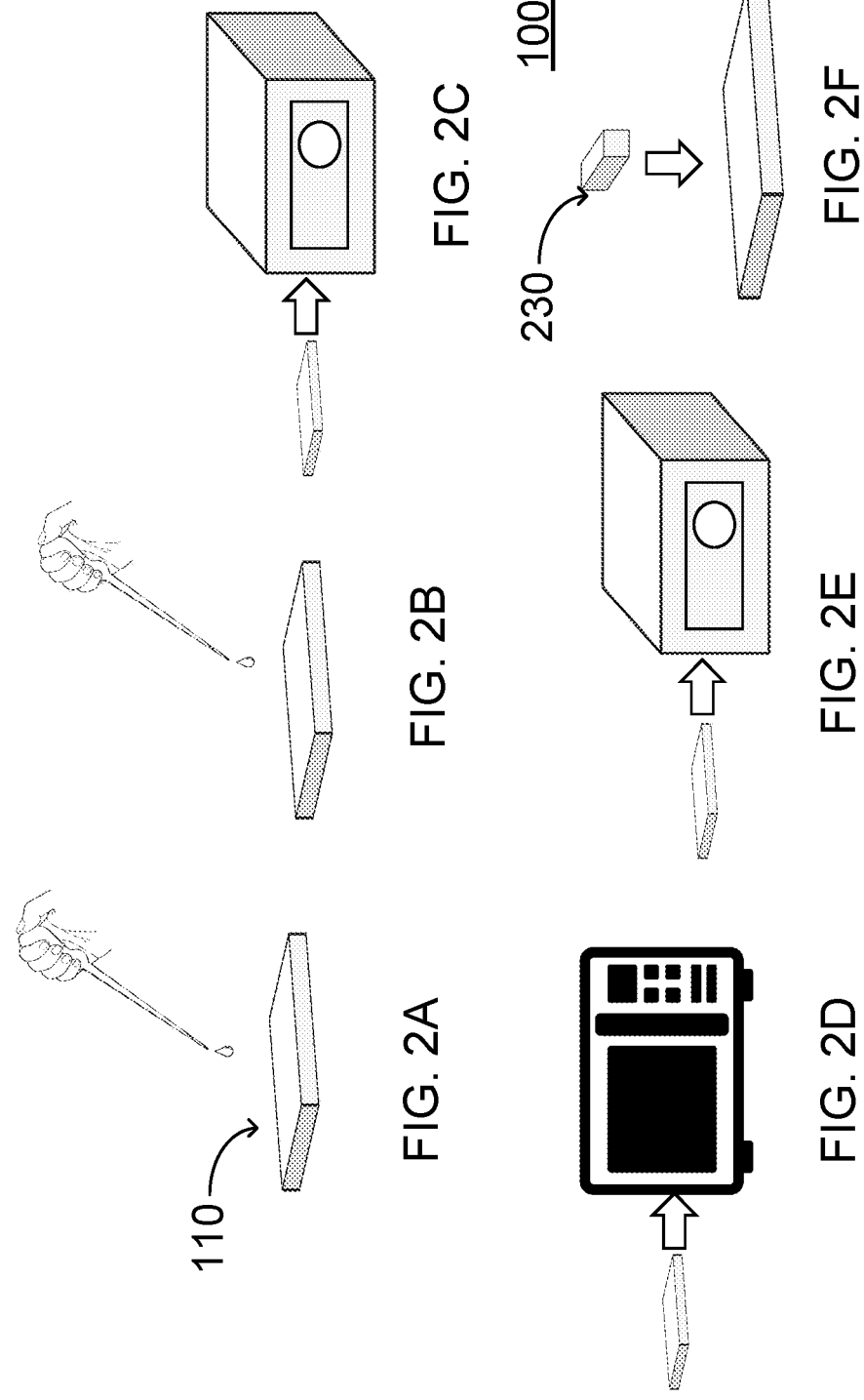
FIGS. 2A-2F are schematic diagrams showing the pretreatment procedures of the detection method for low-concentration metal ions in solution according to the present invention.

FIG. 1 shows a schematic diagram of the operation of the detection method for low-concentration metal ions in solution according to the first preferred embodiment of the present invention. The detection method of the present invention utilizes a field effect transistor 100, which comprises a substrate 110, a gate 120, a source 130, a drain 140, an insulation layer 150 and a gate oxide 160. The operation is: making the solution 210 to be tested contact the field effect transistor 100, that is, the solution 210 to be tested is added to a microfluidic device 230 connected to the gate oxide 160 and the gate 120; then, applying a gate bias $V_G$ to the gate 120; then, measuring a first electronic signal between the source 130 and the drain 140, and the first electronic signal is a first drain current $I_{DS}$, a drain-source bias $V_{DS}$, an inductance or a resistance and etc. In this preferred embodiment, the purpose is to measure the value of the gate bias $V_G$ when the drain current $I_{DS}$ is detected to be a specific value ($10^{-8}$ A in this preferred embodiment).

In other words, it can be considered as a detection chip when the field effect transistor 100 cooperates with the microfluidic device 230.

Then, the same operation is applied to a control solution to obtain the second gate bias $V_G$ and the second electronic signal (i.e., the second drain current $I_{DS}$). Then, the measured second gate bias $V_G$ is subtracted from the first gate bias $V_G$ to obtain an electronic signal difference, that is, the voltage difference $\Delta V$.

The control solution here is employed as a reference for calibration, and the present invention is subjected to a solution with low-concentration metal ions. After obtaining the voltage difference $\Delta V$ according to the detection method of the present invention, it can be inferred whether the metal ions concentration of the solution 210 to be tested is higher or lower than that of the control solution.

In practical operations, the metal ions concentration of the solution 210 to be tested from the manufacturer may not be the same for each batch, but it is only necessary to obtain a as long as the solution of a certain batch meets the usage standard (without defects), the solution of this certain batch can be considered as the control solution.

Even if the metal ions concentration of the control solution is unknown, it can be determined that the control solution meets the standard on the assumption that there are no defects after the usage of the control solution. Accordingly, it can be judged whether the solution 210 to be tested meets the usage standard according to the voltage difference $\Delta V$. The tedious and expensive sophisticated detections will not be necessary.

One of the points of the present invention is to save cost and rapidly judge whether the metal ions concentration of an unknown solution 210 to be tested meets the usage standard by using the concept of relative comparison. Even the metal ions concentration of the control solution is uncertain, it's still possible to rapidly judge whether the solution 210 to be tested meets the standard or not. The acceptance difficulty and detection cost of this compound can be reduced.

Theoretically, the metal ions concentration of the solution corresponds to the bias applied to the gate 120 to a certain extent. On the premise that the drain current reaches a predetermined value, the gate bias $V_G$ required to be applied is greater as the metal ions concentration in the solution is greater. Namely, the greater voltage difference is equivalent to the higher metal ions concentration in the solution 210 to be tested.

Preferably, assuming that the metal ions concentration of the control solution and the corresponding second gate bias $V_G$ can be regarded as known when the number of experiments is quite sufficient, it is only necessary to control the first electronic signal to be equal to the second electronic signal, that is, to control the drain current $I_{DS}$ to be equal to $10^{-8}$ A, then the second gate bias $V_G$ and the calculated voltage difference $\Delta V$ can be directly obtained, even regarding different solutions 210 to be tested (not detected before).

Preferably, the solution 210 to be tested comprises organic matter. Compared with other detection methods, the present invention can exhibit the advantages of rapid and convenient detection.

Preferably, the field effect transistor 110 is selected from a group consisting of a carbon nanotube field effect transistor, a graphene field effect transistor, a nanoplate field effect transistor and a nanowire field effect transistor.

Furthermore, the present invention is especially directed to the solutions of strong acid and strong alkali, particularly to the solution 210 to be tested of which the original pH value is greater than or equal to 9, or is less than or equal to 4.

Furthermore, before the solution 210 to be tested is added to the microfluidic device 230 to contact the field effect transistor 100, the respective original pH values of the solution to be tested and the control solution need to be adjusted to be the same, which is generally between 4 and 9 (greater than 4 and less than 9). Accordingly, errors caused by hydrogen ions ($H^+$) and hydroxide ions ($OH^-$) can be avoided.

Preferably, for the specific solution to be tested, both the temperatures of the solution to be tested and the control solution need to be adjusted to the specific range before the solution 210 to be tested is added to the microfluidic device 230 to contact the field effect transistor 100, and the specific range is 10° C.-80° C. Preferably, for the specific solution, the specific range is 60° C.-70° C.

In detail, the purpose of the microfluidic device 230 is to perform detection with a small amount of solution. Specifically, the microfluidic device 230 is not an essential component, and a larger amount of solution will be required in case of no microfluidic device 230.

Please refer to FIGS. 2A-2F, which are schematic diagrams showing the pretreatment procedures of the detection method for low-concentration metal ions in solution according to the present invention. Please refer to FIG. 1 for component symbols, which will not be repeated here. The detection chip (the field effect transistor 100 and the microfluidic device 230) of the present invention needs a series of pretreatments before it can be used. First, in FIG. 2A, the field effect transistor 100 is cleaned with 99% alcohol, the purpose is to employ alcohol to remove organic molecules on the surface; then, in FIG. 2B, the field effect transistor 100 is repeatedly cleaned with deionized water, the purpose is to remove organic molecules and alcohol on the surface; then, in FIG. 2C, the surface of the field effect transistor 100 is cleaned (using $O_2$ plasma or piranha solution) to remove residual impurities on the surface; then, in FIG. 2D, the field effect transistor is placed in an oven at 120 degrees Celsius for 10 minutes, and is heated to remove the residual moisture on the surface; then, in FIG. 2E, the surface of the field effect transistor 100 is cleaned again (using $O_2$ plasma or piranha solution) to leave no impurities on the surface as much as possible; then, in FIG. 2F, finally, the microfluidic device 230 is attached on the surface of the field effect transistor 100 to complete the pretreatments. It should be noted that the procedures in FIGS. 2A and 2B can be repeated according to the actual requirements, and the procedures in FIGS. 2A and 2B can also be performed again after the step in FIG. 2C.

Figure 3B:
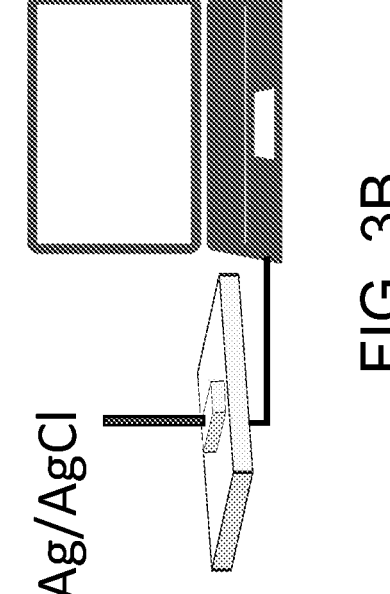
FIGS. 3A-3B are schematic diagrams showing the detection procedures of the detection method for low-concentration metal ions in solution according to the first preferred embodiment of the present invention.
Figure 3A:
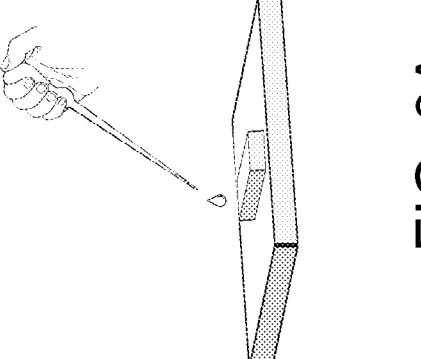

Please refer to FIGS. 3A-3B, which are schematic diagrams showing the detection procedures of the detection method for low-concentration metal ions in solution according to the first preferred embodiment of the present invention. Please refer to FIG. 1 for component symbols, which will not be repeated here. First, in FIG. 3A, the solution 210 to be tested or the control solution is dropped into the microfluidic device 230 of the chip with a 100 μL quantitative dropper (pipette); then in FIG. 3B, in this preferred embodiment, the reference electrode Ag/AgCl is employed as the gate 120 of the detection chip to cooperate with the microfluidic device 230 for operation. When the drain current $I_{DS}$ is $10^{-8}$ A, the first gate bias $V_G$ and the second gate bias $V_G$ are detected. Specifically, between dropping different samples (solution to be tested or control solution), it is necessary to clean the microfluidic device 230 with at least 15 times of displacement (the volume of the microfluidic device 230 is about 20 μL in the present invention), so as to ensure that residues from the previous batch of sample have been washed away. Moreover, it is necessary to soak the reference electrode in deionized water and clean it after the detection.

Please refer to FIG. 4, which is a flowchart illustrating a detection method for low-concentration metal ions in solution according to the first preferred embodiment of the present invention. Please refer to FIG. 1 for component symbols, which will not be repeated here. First, performing Step C1, providing a field effect transistor 100; then, performing Step C2, adjusting an original pH value of a solution 210 to be tested to a specific pH value; then, performing Step C3, making the solution 210 to be tested contact a gate oxide 160 of the field effect transistor 100; then, performing Step C4, applying a first gate bias $V_G$ to a gate 120 of the field effect transistor 100; then, performing Step C5, measuring a first electronic signal (i.e. a first drain current $I_{DS}$) between a source 130 and a drain 140 of the field effect transistor 100.

As the aforesaid method, after the solution 210 to be tested is replaced with the control solution, the corresponding second gate bias $V_G$ and the second electronic signal (i.e., the second drain current $I_{DS}$) will be generated.

Then, the following method is performed: first, adjusting the first gate bias $V_G$ and the second gate bias $V_G$ until the first electronic signal is equal to the second electronic signal, that is, adjusting the first gate bias $V_G$ and the second gate bias $V_G$ when the first drain current $I_{DS}$ and the second drain current $I_{DS}$ are equal to $10^{-8}$ A; then, subtracting the second bias $V_G$ from the first bias $V_G$ to obtain a voltage difference $\Delta V$; then, judging a metal ions concentration of the solution 210 to be tested according to the voltage difference $\Delta V$.

The metal ions concentration here does not need to be accurately known. Because in this chemistry detection in the solutions used in semiconductor industry, it is necessary to judge whether the solution 210 to be tested can be used or not, and the judgment is determined that the metal ions concentration cannot be used if it exceeds a specific value. Assuming that the metal ions concentration of the control solution is determined to be the upper limit that can be used, it is only necessary to know whether the metal ions concentration of the solution 210 to be tested is greater than the metal ions concentration of the control solution.

Figure 5:
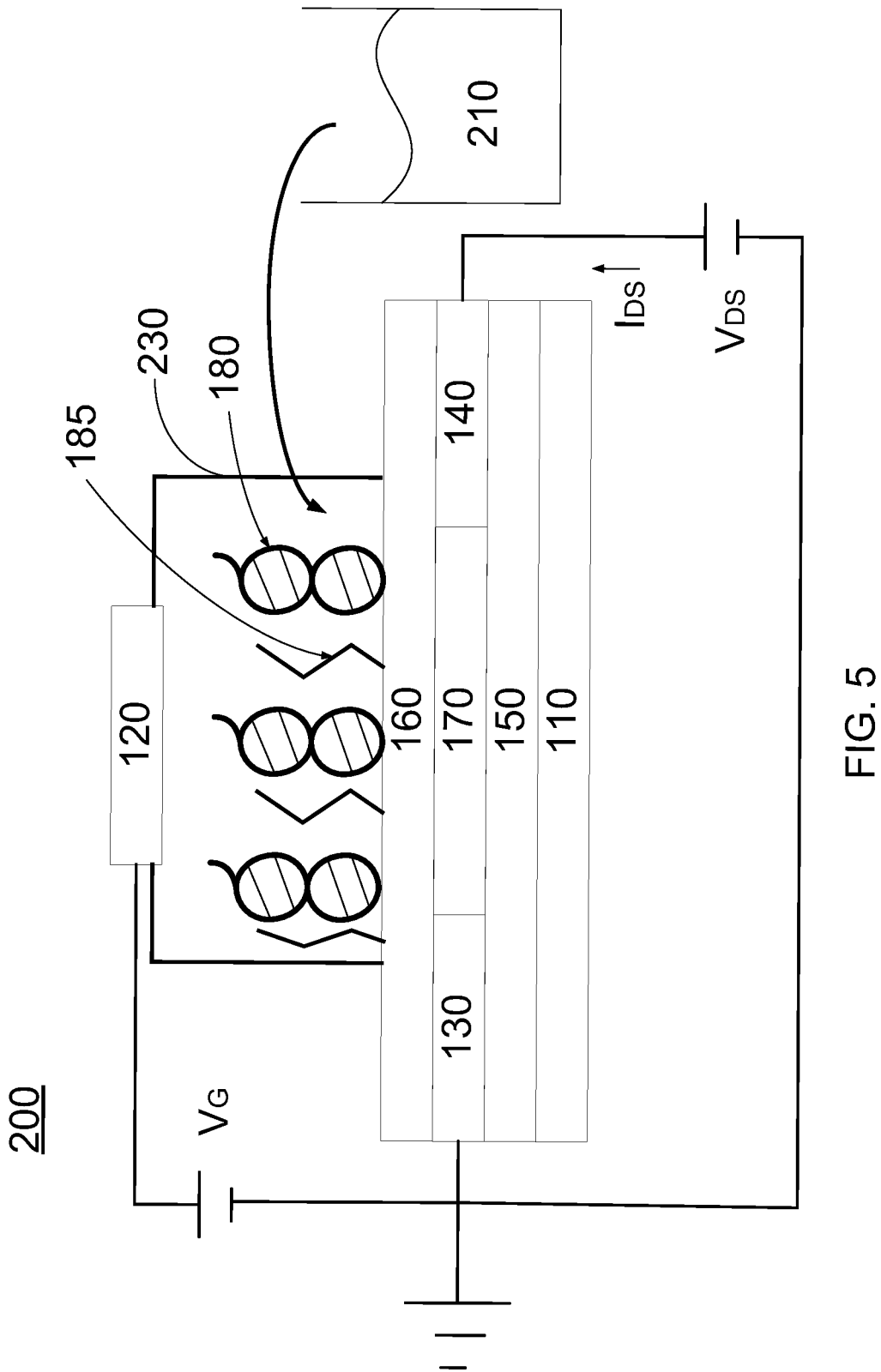
FIG. 5 shows a schematic diagram of the operation of the detection method for low-concentration metal ions in solution according to the second preferred embodiment of the present invention.

FIG. 5 shows a schematic diagram of the operation of the detection method for low-concentration metal ions in solution according to the second preferred embodiment of the present invention. Please refer to FIG. 1 for component symbols, which will not be repeated here. The difference between this embodiment and the first preferred embodiment is: a first functional group 180 for attracting or adsorbing metal ions of the solution 210 to be tested and a second functional group 185 for resisting non-specific adsorption are arranged on a gate oxide 160 of a field effect transistor 100. In other words, resisting non-specific adsorption here refers to preventing the influence to the electronic signals caused by other ions except the metal ions to be attracted or adsorbed by the first functional group 180. Preferably, the first functional group 180 may be an aptamer or a dye; the second functional group 185 may be PEG (Polyethylene Glycol) or a Zwitterion. Compared with the first preferred embodiment, the first functional group 180 possesses the characteristic of selectively attracting specific ions; the second functional group 185 not only is a neutral structure but also possesses a glycosyl group, which can generate hydrogen bonds with water without affecting the distribution of ions in solution, the electric field of the target object and the carrier distribution in the channel, and can improve the hydrophilicity of the chip surface. For instance, as the aptamer can only attract iron ions, the first electronic signal and the second electronic signal will be generated by iron ions, correspondingly. The second functional group 185 forms a protective film on the surface, thereby preventing non-specific adsorption (non-iron ions adsorption), and thus avoiding distortion of detection result. Preferably, in the first electronic signal and the second electronic signal in the first preferred embodiment, the electronic signals are generated by all types of metal ions. In this preferred embodiment, the corresponding first functional group 180 can be configured to cooperate the second functional group 185 according to the requirements in this preferred embodiment to obtain the concentration of specific type of metal ions in the solution 210 to be tested. The detection method is similar as the method of the first preferred embodiment, and will not be repeated here.

Furthermore, although in this preferred embodiment, the first functional group 180 and the second functional group 185 are both arranged on the gate oxide 160. However, either of them can also be solely arranged according to different requirements, and is not limited thereto.

Figure 6:
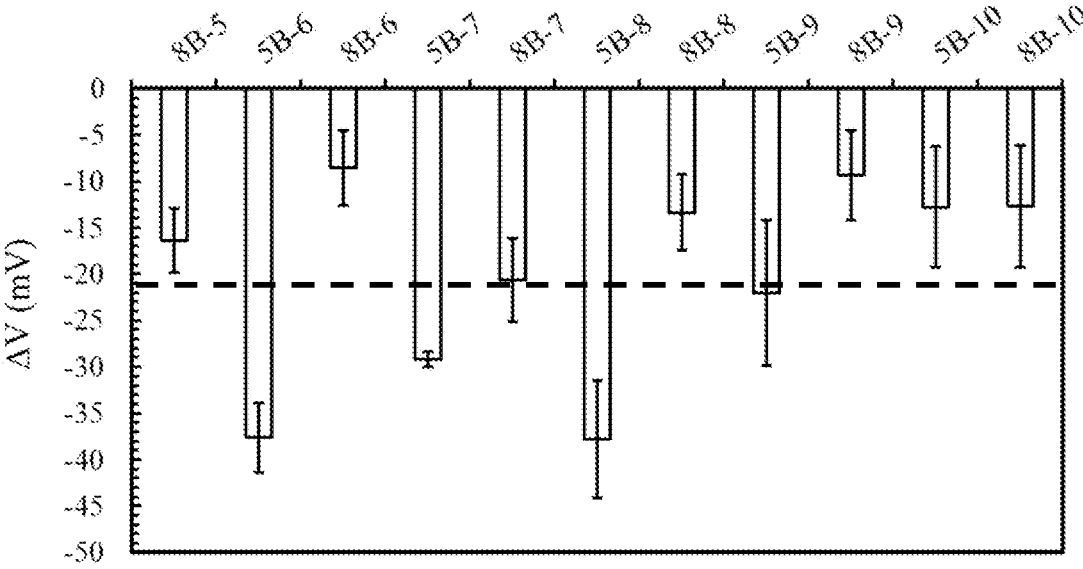
FIG. 6 shows a graph showing the first result of the detection method for low-concentration metal ions in solution according to the second preferred embodiment of the present invention.

FIG. 6 shows a graph showing the first result of the detection method for low-concentration metal ions in solution according to the second preferred embodiment of the present invention. Please refer to FIG. 1 for component symbols, which will not be repeated here. The vertical axis in the figure represents the voltage difference ΔV (mV), and 8B-5, 8B-6, 8B-7, 8B-8, 8B-9, 8B-10 in the horizontal axis are 6 samples of the first batch of solution to be tested; 5B-6, 5B-7, 5B-8, 5B-9, 5B-10 are 5 samples of the second batch of solution to be tested. 5B and 8B are two different batches of chemicals (organic solutions). The threshold value (dotted line) is determined to be −20 mV here. The reason of −20 mV is that the voltage differences ΔV (voltage shift, that is, the strip) of most of 5B exceed −20 mV, and it is also larger than error values (error bar, the I symbol in each strip) of most of 8B, which can effectively distinguish whether the sample is eliminated or not, so the threshold is determined at −20 mV. The dotted line in the said figure is the threshold value of the detection result. If it exceeds this line, it can be judged that the sample possesses a higher metal ions concentration, and the sample can be eliminated to reduce the risk of poor yield.

Therefore, it can be known that the voltage differences ΔV generated by the 8B samples are basically less than −20 mV, and the batch is usable; the voltage differences ΔV generated by the 5B samples are basically greater than −20 mV, and the batch is not usable.

Figure 7:
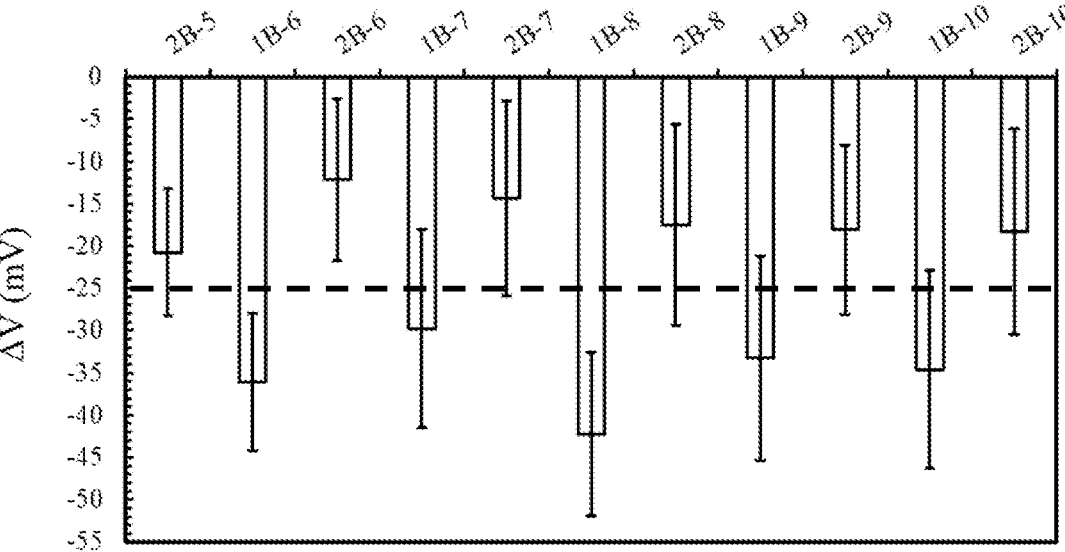
FIG. 7 shows a graph showing the second result of the detection method for low-concentration metal ions in solution according to the second preferred embodiment of the present invention.

FIG. 7 shows a graph showing the second result of the detection method for low-concentration metal ions in solution according to the second preferred embodiment of the present invention. Please refer to FIG. 1 for component symbols, which will not be repeated here. The vertical axis in the figure represents the voltage difference ΔV (mV), and 1B-6, 1B-7, 1B-8, 1B-9, 1B-10 in the horizontal axis are 5 samples of the third batch of solution to be tested; 2B-5, 2B-6, 2B-7, 2B-8, 2B-9, 2B-10 are 6 samples of the fourth batch of solution to be tested. 1B and 2B are two different batches of chemicals (organic solutions). As regarding the results of 1B and 2B, the threshold value is determined at −25 mV. If it is determined below −25 mV, although 1B can be completely eliminated, the actual detected value may exceed the threshold to result that all samples are eliminated due to the large error values of 2B. If the threshold value is too high, the proportion of false negatives will increase, so in order to effectively distinguish between two batches of solutions to be tested, the threshold value is determined to be −25 mV.

It should be understood that the first preferred embodiment will also result similarly to those shown in FIGS. 6-7, but the objects of comparison are all metal ions rather than specific metal ions in the second preferred embodiment, so details are omitted here.

The present invention discloses a detection method for low-concentration metal ions in solution, which avoids damage of strong acids and strong alkalis to the field effect transistors (FET) while using a control solution as a reference for calibration. By adjusting the electronic signals (resistance, inductance, current, voltage, etc.) generated by the two to be the same, the voltage difference therebetween is employed to quantitively and properly infer the metal ions concentration of the solution to be tested.

Above are only preferred embodiments of the present invention, and it should be noted that to any persons who are skilled in the art, improvement and modification which is easily derived should be covered by the protected scope of the application. Thus, the protected scope of the application should go by the subject claims, including the improvement and the modification.

What is claimed is:

1. A detection method for low-concentration metal ions in solution, comprising:
providing a field effect transistor;
adjusting an original pH value of a solution to be tested to a specific pH value;
making the solution to be tested contact a gate oxide of the field effect transistor;
applying a first gate bias to a gate of the field effect transistor; and
measuring a first electronic signal between a source and a drain of the field effect transistor;
adjusting an original pH value of a control solution to the specific pH value;
making the control solution contact the gate oxide of the field effect transistor;
applying a second gate bias to the gate of the field effect transistor; and measuring a second electronic signal between the source and the drain of the field effect transistor.

2. The detection method for low-concentration metal ions in solution according to claim 1, wherein the solution to be tested comprises an organic solvent.

3. The detection method for low-concentration metal ions in solution according to claim 1, wherein the original pH value of the solution to be tested is greater than or equal to 9, or is less than or equal to 4.

4. The detection method for low-concentration metal ions in solution according to claim 1, wherein the field effect transistor is selected from a group consisting of a carbon nanotube field effect transistor, a graphene field effect transistor, a nanoplate field effect transistor and a nanowire field effect transistor.

5. The detection method for low-concentration metal ions in solution according to claim 1, further comprising:

adjusting the first gate bias and the second gate bias until the first electronic signal is equal to the second electronic signal;

subtracting the second bias from the first bias to obtain a voltage difference; and judging a metal ions concentration of the solution to be tested according to the voltage difference.

6. A detection method for low-concentration metal ions in solution, comprising:

providing a field effect transistor;

adjusting an original pH value of a solution to be tested to a specific pH value;

making the solution to be tested contact a gate oxide of the field effect transistor;

applying a first gate bias to a gate of the field effect transistor; and measuring a first electronic signal between a source and a drain of the field effect transistor;

adjusting an original pH value of a control solution to the specific pH value;

making the control solution contact the gate oxide of the field effect transistor;

applying a second gate bias to the gate of the field effect transistor; and measuring a second electronic signal between the source and the drain of the field effect transistor;

wherein a first functional group for attracting or adsorbing metal ions of the solution to be tested and a second functional group for resisting non-specific adsorption are arranged on the gate oxide.

7. The detection method for low-concentration metal ions in solution according to claim 6, wherein the original pH value of the solution to be tested is greater than or equal to 9, or is less than or equal to 4.

* * * * *